(12) United States Patent
Betz et al.

(10) Patent No.: US 10,408,792 B2
(45) Date of Patent: Sep. 10, 2019

(54) MASS SPECTROMETER WITH TANDEM ION MOBILITY ANALYZERS

(71) Applicant: Bruker Daltonik GmbH, Bremen (DE)

(72) Inventors: Thomas Betz, Hamburg (DE); Melvin Andrew Park, Billerica, MA (US); Mark Ridgeway, Stow, MA (US)

(*) Notice: Subject to any disclaimer, the term of this patent is extended or adjusted under 35 U.S.C. 154(b) by 0 days.

(21) Appl. No.: 16/268,214

(22) Filed: Feb. 5, 2019

(65) Prior Publication Data

US 2019/0170689 A1 Jun. 6, 2019

Related U.S. Application Data

(63) Continuation of application No. 15/603,600, filed on May 24, 2017, now Pat. No. 10,241,079.

(51) Int. Cl.
| | |
|---|---|
| H01J 47/00 | (2006.01) |
| G01N 27/62 | (2006.01) |
| H01J 49/00 | (2006.01) |

(52) U.S. Cl.
CPC .......... *G01N 27/622* (2013.01); *H01J 49/004* (2013.01)

(58) Field of Classification Search
CPC ...... G01N 27/622; H01J 49/00; H01J 49/004; H01J 49/0081; H01J 49/02; H01J 49/06; H01J 49/061; H01J 49/062
USPC .......................... 250/281, 282, 283, 286, 290
See application file for complete search history.

(56) References Cited

U.S. PATENT DOCUMENTS

| | | | | |
|---|---|---|---|---|
| 2007/0278397 A1* | 12/2007 | Bateman | ............... | G01N 27/622 250/286 |
| 2011/0121170 A1* | 5/2011 | Park | ...................... | G01N 27/622 250/282 |
| 2015/0069228 A1* | 3/2015 | Park | ...................... | G01N 27/624 250/282 |
| 2017/0178887 A1* | 6/2017 | Park | ...................... | G01N 27/622 |

* cited by examiner

*Primary Examiner* — Jason L McCormack
(74) *Attorney, Agent, or Firm* — Benoit & Côté Inc.

(57) ABSTRACT

The invention proposes a mass spectrometer comprising two ion mobility analyzers in tandem arrangement, of which at least one is a trapped ion mobility spectrometer (TIMS), and an ion gate which is located between the two ion mobility analyzers, and use thereof wherein ions are selectively transferred between the two ion mobility analyzers by adjusting the transmission of the ion gate while ions are separated in time according to ion mobility in the first ion mobility analyzer.

11 Claims, 5 Drawing Sheets

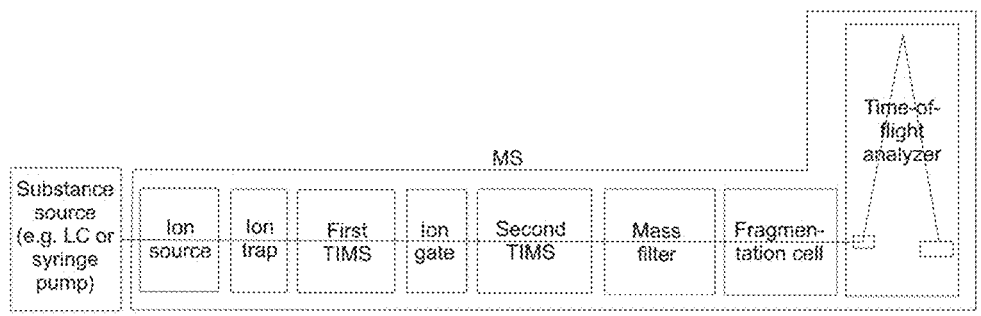
FIGURE 7
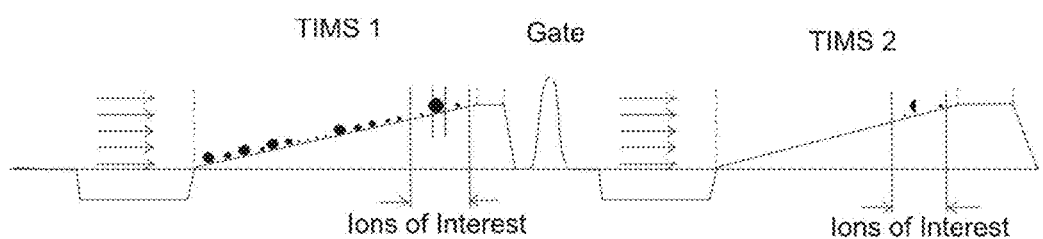
FIGURE 8
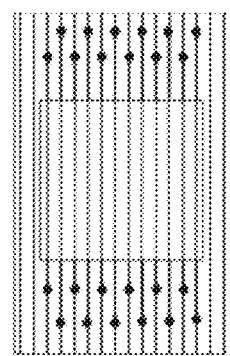 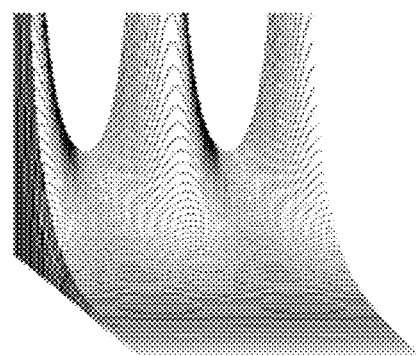
FIGURE 9   FIGURE 10

MASS SPECTROMETER WITH TANDEM ION MOBILITY ANALYZERS

BACKGROUND OF THE INVENTION

Field of the Invention

The invention relates to mass spectrometers with tandem ion mobility analyzers, in particular comprising built-in trapped ion mobility spectrometry (TIMS) analyzers, and corresponding methods for separating ions according to their mobility for detailed substance analyses.

Description of the Related Art

U.S. Pat. No. 7,838,826 B1 (M. A. Park, 2008) presents a small ion mobility analyzer/spectrometer which has become known under the acronym "TIMS" analyzer/spectrometer (TIMS=trapped ion mobility spectrometry). The terms ion mobility analyzer and spectrometer are used interchangeably here. A TIMS analyzer comprises a gas flow that drives ions against a counter-acting electric field barrier such that the ions are at first trapped along the axis of the TIMS analyzer. The ions are confined in the radial direction by an electric RF field. After transferring ions from an ion source to the electric field barrier, the height of the electric field barrier or the gas velocity is adjusted such that ion species are released from the electric field barrier in the sequence of their mobility.

Commonly, the length of the ion mobility separation unit of a TIMS analyzer amounts to about five centimeters only. In a small tube with an inner diameter of about eight millimeters, a radial RF quadrupole field is generated to hold ions near to the axis. A gas flow inside a tube drives ions entrained in the gas flow against a ramped counter-acting electric DC field barrier where the ions are trapped and separated according to their mobilities at locations on the field ramp at which the friction force of the moving gas equals the counter-acting force of the electric DC field on the ramp. After loading the TIMS with ions, the height of the electric DC field barrier is decreased; this scan releases the ion species in the sequence of their mobility. Unlike many other trials to build small ion mobility spectrometers, the small device by M. A. Park has already achieved, with reduced scan speeds, ion mobility resolutions up to $R_{mob}$=400, which is extraordinarily high.

FIG. 1 outlines schematically a common TIMS analyzer and its operation. Entrained by a gas (7), ions (6) from an electrospray ion source (not shown) are introduced via capillary (8) into a first chamber of a vacuum system. A repeller plate (9) drives the ions (6) into an entrance funnel (10) of the mobility analyzer. Ion funnels (10, 12) usually are built as a stack of apertured diaphragms the openings of which taper to smaller diameters thus forming an inner volume in the shape of a funnel. Two phases of an RF voltage are applied alternately to the diaphragms to build up a pseudopotential which keeps the ions away from the funnel walls. The ions are driven to and through the narrow end of the first funnel (10) into the TIMS tube (11) by an axial gas flow (14) and optionally by an additional DC potential gradient along the diaphragms.

The axial gas flow (14) through the TIMS tube (11) is laminar and shows, in radial direction, a substantially parabolic velocity distribution. Nitrogen may serve as a preferred gas. The vacuum conditions around the TIMS tube (11) are chosen such that the maximum gas velocity amounts to about 100 to 150 meters per second, at a pressure of a few hectopascals. This velocity is only achieved near the axis. Further off axis, the velocity is considerably smaller, as indicated by the arrows (14) in FIG. 1.

The first funnel (10) guides the ions into the TIMS tube (11) forming a tunnel with internal RF quadrupole field in radial direction. The TIMS tunnel (11) comprises a stack of thin electrodes with central holes which form a circular tube arranged around the z-axis of the device. The thin electrodes are separated by insulating material closing the gaps between the electrodes around the tube. The electrodes of the TIMS tube (11) are segmented into quadrants (1, 2, 3, 4), to allow for the generation of a radially confining quadrupolar electric RF field inside. The quadrants (1, 2, 3, 4) of the tube electrodes are shown at the top of FIG. 1 with equipotential lines of the quadrupolar RF field inside the tube at a given time. It should be mentioned here that the design of a quadrupole tunnel does not necessarily consist of metal electrode sheets; there are a lot of different possibilities including stacked PCB boards or even a rolled PCB board with printed electrodes.

Inside the TIMS tunnel (11), the ions are blown by the gas flow (14) against an axial electric DC field barrier. In the center part of FIG. 1, the profile of the axial electric DC field barrier is shown for three phases of a scan. Between z locations (20) and (23), the electric DC field increases linearly, generated by a quadratically increasing electric potential. Between z locations (23) and (24), the electric DC field remains constant, forming a plateau of the electric DC field barrier, generated by a linear increase of the electrical potential. In a simple device, for instance, the complete field profile can be generated by a single voltage, applied to the diaphragm electrode at location (24), and divided by precision resistors along the diaphragm electrodes of the TIMS tube (11). The resistors between location (20) and (23) increase linearly, the resistors between (23) and (24) have equal resistance. In more complex devices, non-linear field electric field profiles may be generated, even adjustable DC field profiles, e.g. by digital-to-analog converters (DAC).

The operation of the TIMS analyzer starts with an "ion accumulation phase", accumulating ions on the uppermost electric DC field ramp of the diagram. A voltage difference on the order of 300 volt produces the electric DC field barrier. The ions are blown by the gas flow, symbolically indicated by the arrows (16), against the electric DC field barrier and are stopped there because they cannot surmount the electric DC field barrier. It should be noted that the arrows (16) represent the maximum gas velocity of the parabolic gas velocity distribution (14) within the tube. The ions are accumulated on the rising edge of the electric DC field between locations (20) and (23), where ions of low mobility (mainly heavy ions with large collision cross section) gather in the high field near the upper end of the field ramp, whereas ions of high mobility gather in the low field near the foot of the ramp. The size of the dots represents the abundance of the ions of distinct ion mobility, indicating the strength of the space charge. In the subsequent "scan phase", the supply voltage for the electric DC field barrier is steadily decreased, and ions of increasing mobility can escape towards an ion detector, particularly to a mass analyzer operating as ion detector. In the bottom of the figure, the resulting ion current of the released ion species is shown. The measured total ion current curve i=f(t) presents directly an ion mobility spectrum from low ion mobilities to high ion mobilities.

Regarding the theoretical basis of TIMS, see the research article "Fundamentals of Trapped Ion Mobility Spectrometry", K. Michelmann, J. A. Silveira, M. E. Ridgeway and M. A. Park, J. Am. Soc. Mass Spectrom., (2015) 26: 14-24 (published online: 21 Oct. 2014).

Improvements of the scan modes for TIMS analyzers have been made by application of non-linear scans to achieve a linear mobility scale, a constant resolution along the mobility scale, or a temporal zoom (M. A. Park et al., U.S. Pat. No. 8,766,176 B2). Furthermore, U.S. patent application Ser. No. 15/341,250 (M. A. Park and O. Raether) describes a spatial zoom.

The ion mobility resolution $R_{mob}$ depends on the scan speed. FIG. 3 presents a typical function of the ion mobility resolution versus scan duration. The lower the scan speed, the higher the resolution. As already mentioned, ion mobilities of $R_{mob}$=400 have been achieved with the comparably small devices, using slow scans. Since the ions generated in the ion source are lost during the scan phases, the duty cycle (or the utilization rate of the ions) depends on the ratio of the accumulation time $t_a$ to the scan time $t_s$.

A TIMS analyzer with parallel ion accumulation is described in U.S. patent application Ser. No. 14/614,456 ("Trapping Ion Mobility Spectrometer with Parallel Accumulation", M. A. Park and M. Schubert); it improves the utilization of the ions from the ion source to nearly 100%. TIMS with parallel accumulation does in fact collect and separate by ion mobility all ions of the ion source without any losses of ions, as long as space charge effects do not impair further collection of ions. TIMS with parallel ion accumulation further provides the unique possibility to prolong the ion accumulation duration to find more detectable ion species, thereby even increasing the ion mobility resolution by a corresponding prolongation of the scan time. The ions are collected in an accumulator unit, preferably almost identical to the scanning unit, at a ramp of an electric DC field barrier such that they get spatially separated by their ion mobility along the ramp. Therefore, the accumulated ions are less influenced by space charge than in other types of accumulator units. Of greatest importance, however, is the unique feature of a TIMS analyzer that a longer accumulation period permits to increase the mobility resolution by choosing correspondingly longer mobility scan durations, e.g. 100 milliseconds scan duration with an ion mobility resolution of $R_{mob}$=75 instead of 20 milliseconds scan duration with $R_{mob}$=30. As a consequence of the higher number of ions collected and the better ion mobility resolution, more ion species can be detected and measured. Once an ion mobility scan is completed (optionally after twenty to some hundred milliseconds), the accumulated ions are transferred (in about a millisecond) from the accumulation unit to the scanning unit, and the next ion mobility scan can be started. In total, a skilled practitioner will appreciate that it will be possible to achieve a measurement rate of 300 to 450 ion species per second. If TIMS with parallel ion accumulation is installed in tandem mass spectrometer (MS/MS instrument) an MS-MS instrument, 300 to 450 characteristic fragment ion spectra per second may be measured quantitatively.

The major challenge with TIMS (as with other trapping spectrometers) is space charge. Some improvements for higher amounts of stored ions in selected regions of ion mobility, particularly for ions of low ion mobility, are given in U.S. Pat. No. 9,304,106 B1 (M. A. Park and O. Raether, "High Duty Cycle Trapping Ion Mobility Spectrometer"). The higher loading capacity is based on non-linear electric DC field ramps, with flatter field ramps for ion species of interest, in order to diminish the effect of space charge for these ion species. But for precise ion mobility analyses of low abundant ion species in complex mixtures the influence of the space charge is still too high.

There is still a need for a method to analyze precisely the mobility of low abundant ions in the nearby presence of high abundant ions with high amount of space charge.

SUMMARY OF THE INVENTION

In a first aspect, the invention provides a method for analyzing ions in a mass spectrometer that comprises an ion source, two ion mobility analyzers, of which at least one is a trapped ion mobility spectrometry (TIMS) analyzer, an ion gate that is located between the two ion mobility analyzers and a mass analyzer. The method comprises the steps of: separating ions in time according to mobility in the first ion mobility analyzer; selecting ions of interest by adjusting the transmission of the ion gate during the separation in the first ion mobility analyzer; transferring the selected ions of interest to the second ion mobility analyzer; and separating the transferred ions according to mobility in the second ion mobility analyzer. The step of "selecting ions of interest" comprises that substantially all ions of an ion species of interest or that a portion thereof is selected. The second ion mobility analyzer is preferably a TIMS analyzer, more preferably both ion mobility analyzers are TIMS analyzers.

The separated ions can be further analyzed downstream of the second ion mobility analyzer by acquiring mass spectra or acquiring fragment mass spectra. The acquisition of the fragment mass spectrum preferably comprises selecting precursor ions in a mass filter that is located between the second ion mobility analyzer and a fragmentation cell.

In one embodiment, the second ion mobility analyzer is a TIMS analyzer and the first separation and the selectively transfer are repeated. The second ion mobility analyzer is preferably operated to accumulate the repeatedly transferred ions of interest prior to separating them according to mobility. More preferably, the repeatedly transferred ions are accumulated in an additional ion trap which is located between the ion gate and the TIMS analyzer and used for decoupling the accumulation and the separation in the TIMS analyzer.

In another embodiment, the second ion mobility analyzer is a TIMS analyzer and the transmission of the ion gate is adjusted while the ions are separated in the first ion mobility analyzer such that the total space charge of the ions transferred to the second ion mobility analyzer and/or the local space charge of the transferred ions in the trapping region of the second ion mobility analyzer is below a predetermined threshold.

In another embodiment, the transmission of the ion gate is adjusted while the ions are separated in the first ion mobility analyzer such that the transmission for a highly abundant ion species of interest is lower than the transmission of less abundant ion species of interest. The transmission of the ion gate can be adjusted by varying the duration of opening intervals or by adjusting an effective opening of the ion gate. The latter can be accomplished by varying DC and/or RF voltages supplied to electrodes of the ion gate while the ions are separated in the first ion mobility analyzer, in particular while an ion species is released from an electric field barrier of a first TIMS analyzer.

Any adjustment of the transmission of the ion gate is preferably taken into account in a post-processing of ion mobility spectra and/or mass spectra for evaluating the abundance of ion species and in a graphical representation of ion signals.

In another embodiment, only ions of a single range of mobility are transferred to the second ion mobility analyzer, wherein the single range of mobility is a reduced subset of the full range of mobility. The ion gate is opened and closed once while the ions are separated in the first ion mobility analyzer such that the transferred ions of interest are substantially from the single mobility range. In case the second ion mobility analyzer is a TIMS analyzer, the electric DC field ramp of the TIMS analyzer is preferably adjusted such that the transferred ions of interest of the single mobility range spread substantially over the full width of the electric DC field ramp. In addition, the steps of releasing ions from the first ion mobility analyzer and transferring ions to the second TIMS analyzer can be repeated several times, before the repeatedly accumulated ions are released from the second TIMS analyzer for further analysis.

In another embodiment, ions are transferred from the ion source towards the first ion mobility analyzer and trapped upstream of the first ion mobility analyzer while preceding ions are separated in the first ion mobility analyzer, in particular in an TIMS analyzer.

In a second aspect, the invention provides a method for analyzing ions in a mass spectrometer that comprise an ion source, two ion mobility analyzers, of which at least the second ion mobility analyzer is a trapped ion mobility spectrometry (TIMS) analyzer, a mass filter located between the two ion mobility analyzers and a mass analyzer. The method comprises the steps of: separating ions in time according to mobility in the first ion mobility analyzer; filtering the separated ions according to mass in the mass filter wherein the transmitted mass range of the mass filter varies while the ions are separated in the first ion mobility analyzer; transferring the filtered ions to the second ion mobility analyzer; and separating the transferred ions according to mobility in the second ion mobility analyzer.

The second ion mobility analyzer is preferably a TIMS analyzer, more preferably both ion mobility analyzers are TIMS analyzers.

The mass filter is one of low-pass filter, high-pass filter and a band-pass filter and is preferably operated at a gas pressure above 10 Pascal, most preferably at the operating pressure of one of or both ion mobility analyzers.

The separated ions can be further analyzed downstream of the second ion mobility analyzer by acquiring mass spectra or acquiring fragment mass spectra. The acquisition of the fragment mass spectrum preferably comprises a selection of precursor ions in an additional mass filter that is located between the second ion mobility analyzer and a fragmentation cell.

In a third aspect, the invention provides a mass spectrometer that comprises an ion source, two ion mobility analyzers, of which at least one is a trapped ion mobility spectrometry analyzer (TIMS), an ion gate or a mass filter located between the two ion mobility analyzers and a mass analyzer. The ion gate is configured to vary the transmission of ions during operation of the first mobility analyzer. The mass filter is configured to vary the transmitted mass range during operation of the first mobility analyzer. Preferably, the second ion mobility analyzer is a TIMS analyzer, more preferably both ion mobility analyzers are TIMS analyzers.

The mass spectrometer according to the invention can further comprise an ion trap between the ion gate or mass filter and the second ion mobility analyzer, a fragmentation cell between the second ion mobility analyzer and the mass analyzer and an additional mass filter between the second ion mobility analyzer and the fragmentation cell. The additional mass filter can be a quadrupole mass filter. The mass analyzer of the mass spectrometer can be one of a time-of-flight mass analyzer, a time-of-flight mass analyzer with orthogonal ion injection, a RF ion trap, a DC ion trap (like an orbitrap or cassini-trap) and ion-cyclotron-resonance trap. The fragmentation cell can use at least one of following fragmentation techniques: collision induced dissociation (CID), surface induced dissociation (SID), photodissociation (PD), electron capture dissociation (ECD), electron-transfer dissociation, and electron impact dissociation (EID).

The ion gate is preferably one of an ion-optical einzel lens and a Bradbury-Nielsen grid wherein a DC and/or RF generator is connected to the grid. A Bradbury-Nielsen gate operated with RF voltages presents the additional advantage to reflect ions of high mobility while transmitting ions of low mobility. The mass filter is preferably a Loeb-Eiber filter.

BRIEF DESCRIPTION OF THE DRAWINGS

FIG. 2 shows a schematic overview of a mass spectrometer according to the invention with two TIMS analyzers and an ion gate in between.

FIG. 7 presents an arrangement with an additional ion trap between the ion source and the first TIMS analyzer for parallel ion accumulation and scan.

FIG. 8 presents an operation method in which ions of high abundance within the range of interest are partially transferred from the first TIMS analyzer to the second TIMS analyzer by closing the gate in a suitable time interval during the release of these ions.

FIG. 9 shows a Bradbury-Nielsen grid on a printed circuit board as ion gate.

FIG. 10 shows the distribution of the RF pseudo potential for a section of the Bradbury-Nielsen grid with saddle-like passageways for ions of sufficiently low mobility.

DETAILED DESCRIPTION

Figure 1:
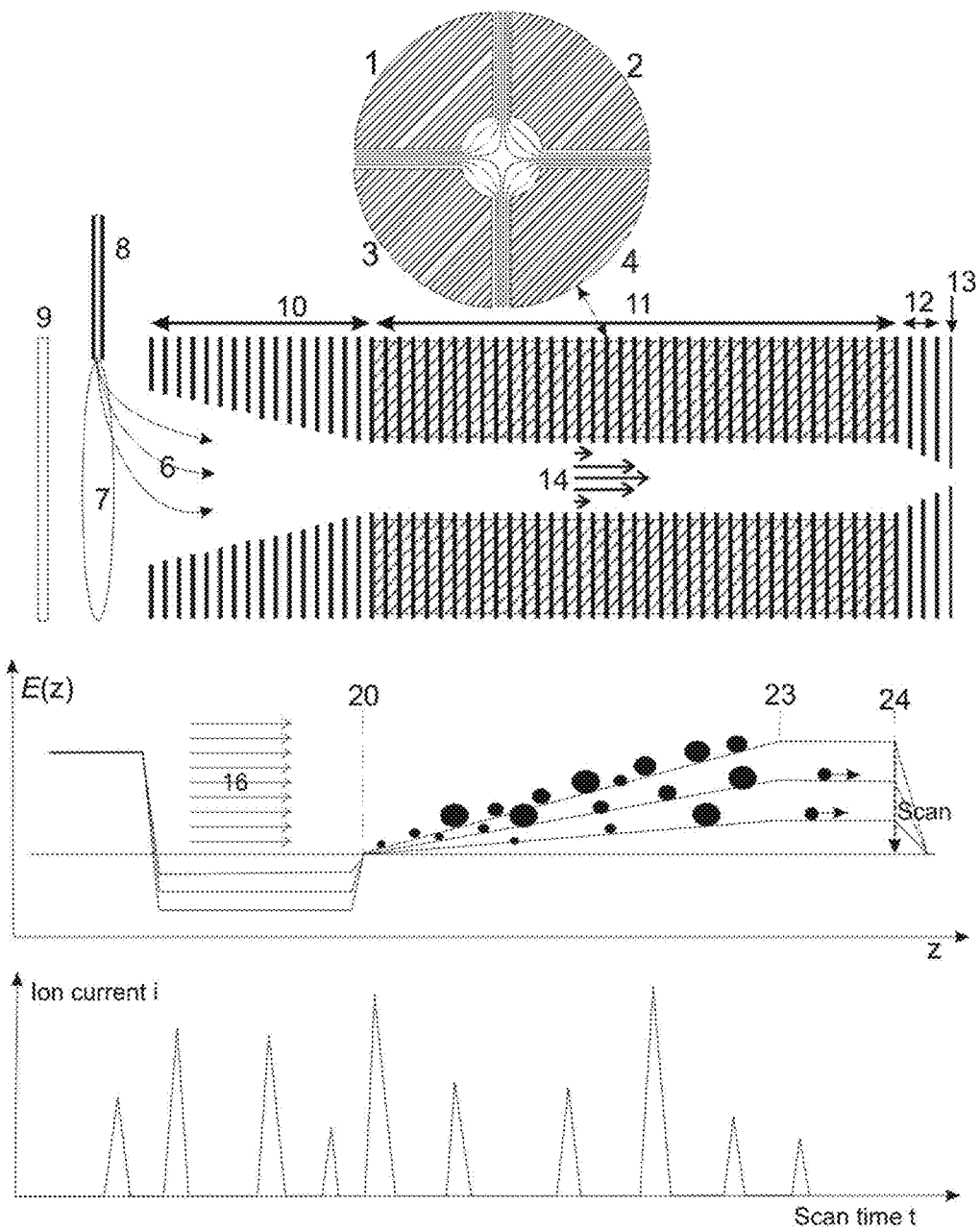
FIG. 1 shows the device and operation of a common trapped ion mobility spectrometry (TIMS) analyzer. Top: Scheme of the TIMS device. Center: The profile of the electric field strength along the z axis. The size of the dots on the electric field ramp reflects their space charge. The scan releases the ion bunches in sequence of their mobilities. Bottom: The ion current of ion pulses separated in time according to mobility, representing an ion mobility spectrum.

The invention provides a method for measuring ion mobility and masses using a mass spectrometer comprising two ion mobility analyzers in a tandem arrangement, at least one of those being a trapped ion mobility spectrometry (TIMS) analyzer, and the ion mobility analyzers being separated by a fast-switching ion gate. The first ion mobility analyzer is scanned and thereby releases ions in sequence of their ion mobility. During the scan, the ion gate is operated such that ions from ion mobility ranges without interest are stopped and ions from mobility ranges of interest are transferred to the second ion mobility analyzer for further analysis. The transferred ions enter the second ion mobility analyzer where they can be analyzed according to their ion mobility. The mass spectrometer then can measure their precise masses; a tandem mass spectrometer even can measure fragment ion spectra for better identification.

In one embodiment, ion pulses of highly abundant ions in the range of interest are, preferably by a suitable opening interval of the ion gate shorter than the ion pulse length, only partially transferred to the second ion mobility analyzer such that the passed ions can be analyzed according to their ion mobility with high ion mobility resolution, undisturbed by space charge. Ions outside the range of interest are substantially reflected in full. It is an advantage of this invention to lower drastically the space charge influence onto the scan of a second TIMS analyzer, and to allow for high amounts of ions in preceding ion mobility analyzers. As a result, the final ion mobility scan has a higher ion mobility resolution, even with much higher amounts of ions, and the mobility spectrum or mobility-mass spectrum is more stable with respect to mobility peaks vs. scan time.

In another embodiment, ions of several ranges of mobility are transferred, by suitable opening the ion gate, to the second ion mobility analyzer during a single scan of the first ion mobility analyzer.

In another embodiment, ions of a single range of mobility only are transferred, by opening the ion gate, to the second ion mobility analyzer. If the second ion mobility analyzer is a TIMS analyzer, then the electric field ramp of this TIMS analyzer can be adjusted such that the ions of the selected single ion mobility range of interest spread approximately over the full width of the electric field ramp. Ions can be accumulated and scanned several times in the first ion mobility analyzer, transferring each time ions of interest to the second ion mobility analyzer, before the ions are scanned from the second ion mobility analyzer for further analysis.

The first ion mobility analyzer can use the drift of an ion bunch through a resting gas, but in a preferred embodiment, two TIMS analyzers are arranged in sequence (TIMS1 and TIMS2). The temporal scan of the TIMS analyzers may be linear or curved, or may be performed with temporal zoom as described in U.S. Pat. No. 8,766,176 B2 cited above. The ramps of the electric field barriers may be curved to lower the space charge at the upper end of the ramp as described in U.S. Pat. No. 9,304,106 B1 cited above.

Figure 2:
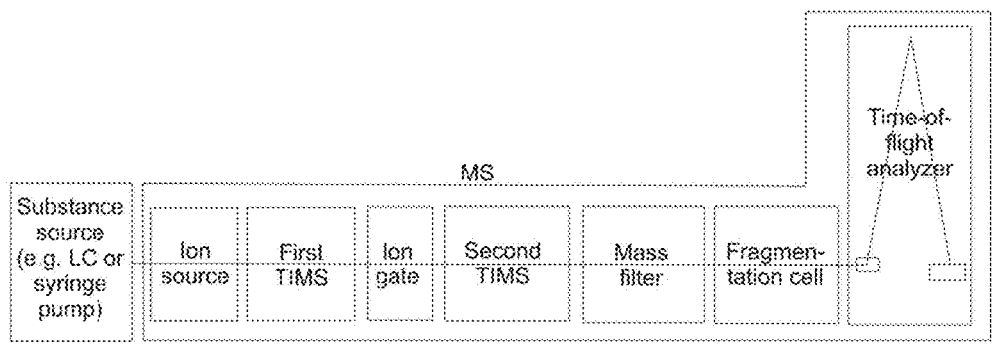

FIG. 2 shows a time-of-flight mass spectrometer with two TIMS analyzers in a tandem arrangement. The first ion mobility analyzer (TIMS 1) may scan a bunch of collected ions, thereby releasing ions in sequence of their ion mobilities. During the scan, the ion gate is alternately opened and closed, closed to reflect (or neutralize) unwanted ions and opened to pass ions in distinct ranges of mobility. In this way, highly abundant ions with their space charge can be reflected in full or at least partially. The passing ions enter the second ion mobility analyzer (TIMS 2) where they can be analyzed according to their ion mobility with high ion mobility resolution, undisturbed by space charge. The mass spectrometer then can measure their precise masses; a tandem mass spectrometer with quadrupole mass filter and time-of-flight analyzer, as presented in FIG. 2, even can measure fragment ion spectra for a better identification of the ion species.

The ions transferred to TIMS 2 may stem from a single range of mobility, or from several ranges, selected by switching the gate accordingly. In one embodiment, ions from a single range of mobility are collected on a flat ramp of TIMS 2, to spread the ions as far as possible along the z axis of TIMS 2. In this mode, ions may be accumulated and scanned in TIMS 1 several times to accumulate as many ions in TIMS 2 as required for an analysis of high quality. If there is a kind of ion with extremely high abundance within the range of interest, only a small portion of these ions may be transferred by reflecting the largest part of these ions. The ion gate preferably switches faster than the temporal width of ion pulses leaving the first ion mobility analyzer. The length of an ion pulse released by the scan is in the order of a millisecond, whereas the switching time for the gate can be below a microsecond; the ion pulse therefore can easily be cut into portions.

Whereas the radially confining RF field of TIMS 2 is preferably quadrupolar in order to achieve a high ion mobility resolution, TIMS 1 may show a tube with higher inner diameter, and/or with radial RF fields of higher multitude, like hexapole, octopole, or dodecapole, or with an RF tunnel. An ion trap can additionally be located upstream of TIMS 1 to accumulate ions from the ion source during the scan of TIMS 1. If the trap can be mass selectively unloaded, even TIMS 1 may be relieved from space charge.

Figure 2A:
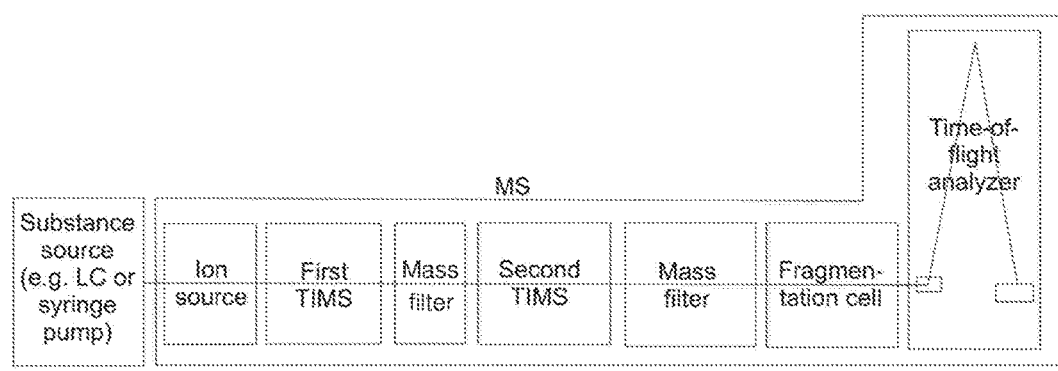
FIG. 2A shows a variation of the system shown in FIG. 2 in which the ion gate is replaced with a mass filter.

FIG. 2A depicts an alternate embodiment to that shown in FIG. 2 in which the ion gate is replaced by a mass filter. In this version of the method, ions are separated in time according to mobility in TIMS 1. The separated ions are then filtered according to mass in the mass filter such that the transmitted mass range of the mass filter varies while the ions are separated in TIMS 1. The filtered ions are then transferred to TIMS 2 which again separates them by mobility. The optional second mass filter and fragmentation cell may thereafter be used, if desired, to further filter the separated ions by mass and/or fragment them prior to their introduction into the mass analyzer.

Figure 3:
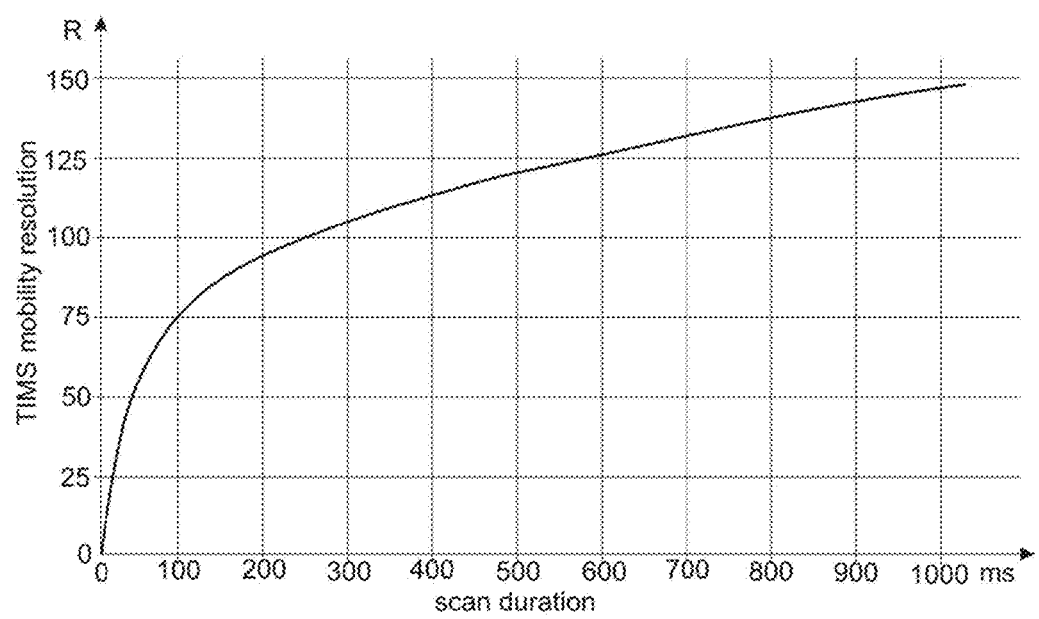
FIG. 3 presents the measured ion mobility resolution $R_{mob}$ for the first TIMS analyzer shown in FIG. 2, given for ions of low mobility ($K \approx 0.5$ m$^2$/Vs), as a function of the scan duration. The scan duration is defined here as the full scan time from low mobilities ($K \approx 0.5$ m$^2$/Vs) to high mobilities ($K \approx 1.0$ m$^2$/Vs). The curve is typical for TIMS.

FIG. 3 presents the measured dependence of the ion mobility resolution for TIMS 1, with ion gate and TIMS 2 open for ion transmission. The measured ion mobility resolution of TIMS 2 is slightly lower due to the slight pressure diminution along the two TIMS devices ($R_{mob}=140$ instead of $R_{mob}=145$ for 1000 milliseconds scan duration).

Figure 4:
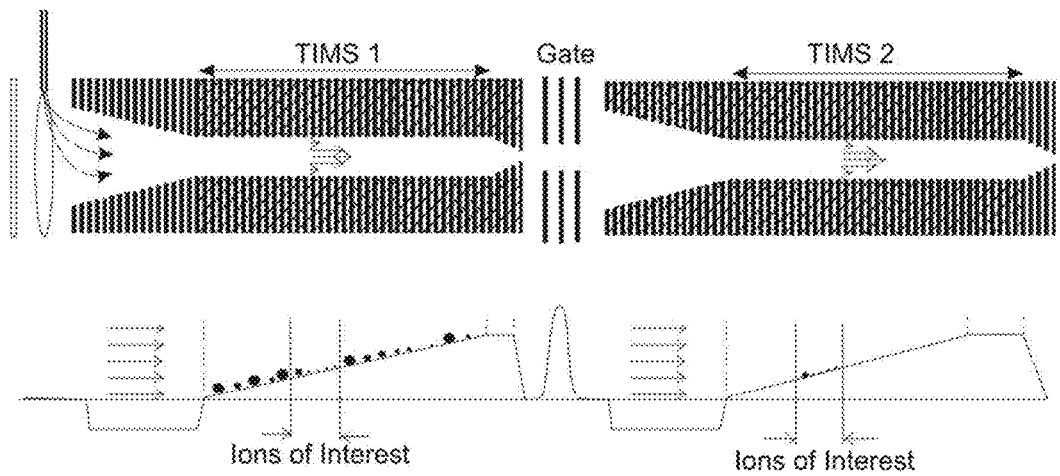
FIG. 4 schematically depicts a device and operation of the device of the invention, with a first TIMS analyzer (TIMS 1), an ion gate, and a second TIMS analyzer (TIMS 2). The diagram below shows ions collected on the field ramp of TIMS1, with a marked range of ion mobility representing the ions of interest. The size of the dots represents the amount of ions of each type, thereby indicating the space charge of these ions. During the scan these ions are selected by the gate and collected on the electric field ramp of TIMS 2. They can be analyzed without space charge disturbance.

FIG. 4 illustrates, in the top part, two tandem TIMS devices (TIMS 1, TIMS 2) separated by an ion gate. In this embodiment, the ion gate is formed as an ion-optical einzel lens. The gate can be switched on and off in less than a microsecond. During the scan of TIMS 1, the gate may be opened and closed in a suitable manner to pick out ions of interest. The ions of interest transferred to TIMS 2 may stem from a single range of mobility, as shown in the bottom part of FIG. 4.

Figure 5:
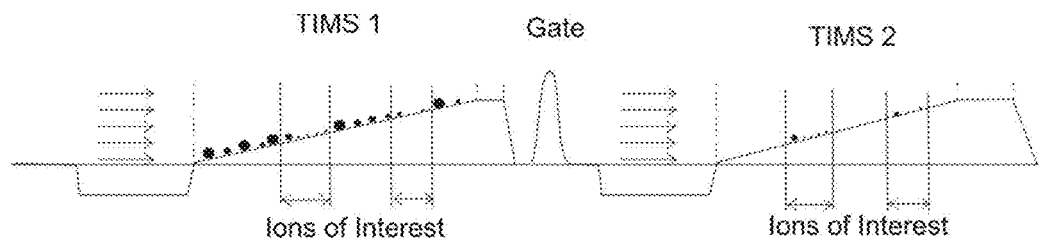
FIG. 5 presents an operation method for transferring ions from two disjoint ranges of ion mobility from the first TIMS analyzer to the second TIMS analyzer by opening the ion gate two times.

FIG. 5 shows a preferred mode of operation with more than one ion mobility ranges of interest. Here, ions of interest from two disjoint mobility ranges are transferred from TIMS 1 to TIMS 2 in a single scan of TIMS 1 by opening and closing the ion gate two times during the single scan of TIMS 1.

Figure 6:
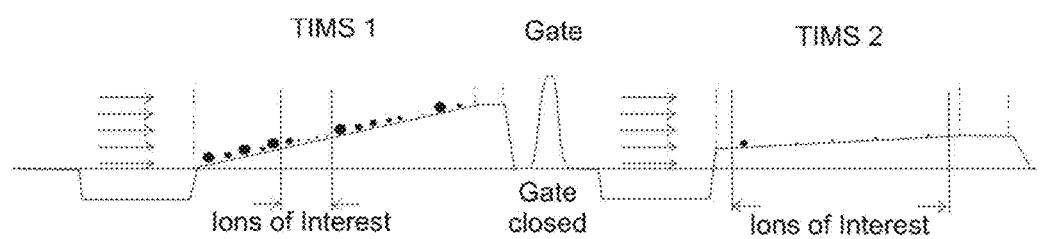
FIG. 6 presents an operation method for transferring ions of interest from the first TIMS analyzer to the second TIMS analyzer wherein the electric DC field ramp of the second TIMS analyzer is matched to collect the ions of interest spatially separated as far as possible. Repeating collection over several scan periods of the first TIMS analyzer can increase the number of ions collected in the second TIMS analyzer.

A special mode of operation is illustrated in FIG. 6. Ions from a single range of mobility are collected on a flat ramp of TIMS 2, to spread the ions as far as possible along the z axis of TIMS 2. In this mode, ions may even be accumulated and scanned in TIMS 1 several times to accumulate as many ions in TIMS 2 as required for an analysis of high quality. Applying a temporal zoom in TIMS 1 can drastically shorten the total scan time of TIMS 1, by a fast scan down to the region of the ions of interest (almost a jump), then scanning slowly the ions of interest, and then jumping down to get rid of the residual high mobility ions. Such a temporal zoom may shorten the total scan duration to about 10 milliseconds, nevertheless achieving a mobility resolution of Rmob>100 in TIMS 1 for neatly cutting out the ions of interest. Accumulating the ions of multiple scans (e.g. 10 scans) in TIMS 2, allows for an ion mobility analysis in TIMS 2 with high ion mobility resolution.

The tandem TIMS devices described up to now have to be loaded with ions from the ion source in an extra time phase, reducing the duty cycle of the instrument. In a preferred embodiment, there may be located an additional ion trap between ion source and TIMS 1 to accumulate ions from the ion source during the scan of TIMS 1, similar to the TIMS with parallel accumulation, described in U.S. patent application Ser. No. 14/614,456 cited above. FIG. 7 presents a scheme of this device with an additional ion trap. The ion trap may be any device capable to store ions. A preferred ion trap is a linear RF quadrupole ion guide, operated with gas at a pressure of some hundred Pascal, with DC barriers at both ends.

Accumulating the ions of multiple scans of TIMS 1 in TIMS 2, leads to the problem that TIMS 2 can't accept ions from TIMS 1 while it is itself scanning. The method has the drawback of a low duty cycle, reduced to 50%. A 100% duty cycle can be achieved for a tandem TIMS device by using a first ion trap between the ion source and TIMS 1 and a second ion trap between the ion gate and TIMS 2. Multiple scans of TIMS 1 (preferably non-linear scans with temporal zoom) can deliver ions of a selected mobility range or selected mobility ranges. These ions are accumulated in the second ion trap, and, when the TIMS 2 is ready, these ions are transferred from the second ion trap to TIMS 2 and there mobility separated. The second ion trap may be any device capable to store ions; however, in a preferred arrangement, a linear RF quadrupole ion guide serves as the ion trap, operated with gas at a pressure of some hundred Pascal, with DC barriers at both ends.

If there is an ion species with extremely high abundance within the ion mobility range of interest, only a small portion of ions of this ion species can be transferred by reflecting, deflecting or neutralizing the largest part of these ions, as shown schematically in FIG. 8. The duration of an ion pulse released by a scan is in the order of one millisecond, whereas the switching time for the gate is below a microsecond; the ion pulse therefore can easily been cut into portions, as indicated symbolically in the figure.

To keep production costs low, TIMS 1 and TIMS 2 can be made identical. However, this is not absolutely required. Whereas the field inside TIMS 2 should be quadrupolar to achieve a high ion mobility resolution, TIMS 1 may show a tube with higher inner diameter, and/or with radial RF fields of higher multitude, like hexapole, octopole, or dodecapole fields. Even stacked ring ion guides may be used. In this way, TIMS 1 can accumulate many more ions, and the scan is less influenced by space charge. A TIMS device of this kind is described in U.S. patent application Ser. No. 15/172,237 (Th. Betz, M. A. Park and O. Raether, 2016).

The ion gate may be a simple ion einzel lens with three apertures, as indicated in FIG. 4. Other embodiments may comprise a Bradbury-Nielsen gate operated with DC voltages. A Bradbury-Nielsen gate with wires which can be alternately supplied with positive and negative voltages is presented in FIG. 9.

Figure 11:
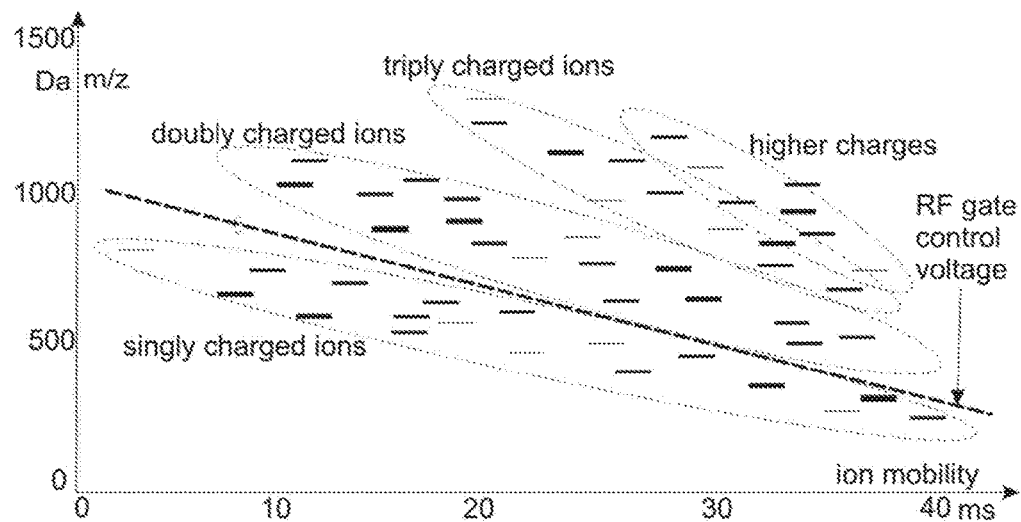
FIG. 11 outlines the release of ion species of different masses and mobilities during a single TIMS scan. With an RF Bradbury-Nielsen grid operated with decreasing voltage (RF gate control voltage) during the TIMS scan, the singly charged ions may be completely suppressed.

In an alternate operation mode, the Bradbury-Nielsen gate is operated with RF voltages, forming reflecting pseudo-potentials around the wires, as illustrated in FIG. 10. This RF Bradbury-Nielsen gate has the additional advantage to reflect ions of low mass (high mobility) while transmitting ions of high mass (low mobility), the limit of transmission depending on the RF voltage on the wires (gate control voltage). This effect may be used in diverse applications. As an example, FIG. 11 depicts schematically mass spectra which are acquired for ion pulses separated according to ion mobility during a scan of TIMS 1. The singly charged ions, forming a band in the lower part of the mass-mobility plot, are quite often not well suited for further analysis. Using an RF Bradbury-Nielsen gate with decreasing RF gate control voltage during the scan of TIMS 1, as indicated by the fat dashed line, keeps the singly charged ions away from TIMS 2. This concept may be generalized such that any undesirable species as for instance chemical background in this range may be separated from desired ion species above the dashed line in FIG. 11.

The arrangement of the invention, as shown in FIGS. 2 and 7, can also be used to investigate the effect of ion manipulations. As an example, an ion species of distinct ion mobility, selected by the ion gate, may be accelerated by 10 to 60 volts between ion gate and TIMS 2. The numerous collisions with the molecules of the gas flow may change the molecular configuration, e.g. by partially unfolding highly folded ions. The resulting change of their collisional cross section may then be analyzed by TIMS 2. As another example, different drift gases may be used in TIMS 1 and TIMS 2, as for instance $N_2$ in TIMS 1 and $CO_2$ in TIMS 2. Or additional gases ("modifiers") may be used in TIMS 2, like $SF_6$ or small organic compound gases.

The invention claimed is:

1. A method for analyzing ions in a mass spectrometer comprising an ion source, first and second trapped ion mobility spectrometry (TIMS) analyzers, a mass filter located between the first and second TIMS analyzers and a mass analyzer located downstream of the second TIMS analyzer, the method comprising the steps of:
   transferring ions from the ion source to the first TIMS analyzer;
   driving the ions transferred to the first TIMS analyzer by a first gas flow against a first counter-acting electric DC field barrier such that the ions are trapped and spatially separated according to their mobilities at different positions along a ramp of the first electric field barrier at which a friction force of the first gas flow equals the counter-acting force of the first electric DC field barrier;

temporally separating ions according to mobility in the first TIMS analyzer by adjusting a height of the first electric DC field barrier or the velocity of the first gas flow;

separating undesirable ion mobility species from ion mobility species of interest by varying the transmitted mass range of the mass filter while the ions are separated in the first TIMS analyzer;

transferring the filtered ions to the second TIMS analyzer;

driving the ions transferred to the second TIMS analyzer by a second gas flow against a second counter-acting electric DC field barrier such that the ions are trapped and spatially separated according to their mobilities at different positions along a ramp of the second electric DC field barrier at which a friction force of the second gas flow equals the counter-acting force of the second electric DC field barrier; and separating the transferred ions according to mobility in the second TIMS analyzer by adjusting a height of the second electric DC field barrier or the velocity of the gas flow.

2. The method according to claim 1, wherein the mass filter is operated at a gas pressure above 10 Pascal.

3. The method according to claim 1, wherein the mass filter is operated at a gas pressure of one of or both TIMS analyzers.

4. The method according to claim 1, wherein the undesirable ion mobility species are singly charged.

5. The method according to claim 1, wherein the undesirable ion mobility species are chemical background.

6. The method according to claim 1, wherein the ions which are separated in the second TIMS analyzer are further analyzed by acquiring mass spectra or fragment mass spectra.

7. A mass spectrometer comprising an ion source, first and second trapped ion mobility spectrometry analyzers (TIMS), a mass filter located between the two ion mobility analyzers and a mass analyzer, wherein the first and second TIMS analyzers each comprise a gas flow and a counter-acting electric DC field barrier configured to spatially separate ions according to their mobilities at different positions along a ramp of the electric field barrier at which a friction force of the first gas flow equals the counter-acting force of the electric DC field barrier and to temporally separate ions according to mobility by adjusting a height of the electric DC field barrier or a velocity of the gas flow, and wherein the mass filter is configured to vary the transmitted mass range during operation of the first TIMS analyzer.

8. The mass spectrometer according to claim 7, wherein the mass filter is one of a low-pass filter, a high-pass filter and a band-pass filter.

9. The mass spectrometer according to claim 8, wherein the mass filter is operated at a gas pressure above 10 Pascal.

10. The mass spectrometer according to claim 8, wherein the mass filter is a Loeb-Eiber mass filter.

11. The mass spectrometer according to claim 7, further comprising a fragmentation cell between the second TIMS analyzer and the mass analyzer.

* * * * *